United States Patent [19]
Drent et al.

[11] Patent Number: 5,359,081
[45] Date of Patent: Oct. 25, 1994

[54] CARBONYLATION OF EPOXIDES

[75] Inventors: Eit Drent; Eric Kragtwijk, both of Amsterdam, Netherlands

[73] Assignee: Shell Oil Company, Houston, Tex.

[21] Appl. No.: 206,293

[22] Filed: Mar. 3, 1994

Related U.S. Application Data

[62] Division of Ser. No. 82,211, Jun. 24, 1993, Pat. No. 5,310,948.

[30] Foreign Application Priority Data

Jun. 29, 1992 [EP] European Pat. Off. ........ 92201940.1

[51] Int. Cl.$^5$ ............................................ C07D 305/12
[52] U.S. Cl. .................................................... 549/328
[58] Field of Search ......................................... 549/328

[56] References Cited

U.S. PATENT DOCUMENTS

| | | | |
|---|---|---|---|
| 2,782,226 | 2/1957 | Seon et al. | 560/189 |
| 3,028,417 | 4/1962 | Eisenmann | 560/179 |
| 3,260,738 | 7/1966 | McClure et al. | 560/179 |
| 4,209,467 | 6/1980 | Kojima et al. | 549/375 |

FOREIGN PATENT DOCUMENTS 1020575 2/1966 United Kingdom .

OTHER PUBLICATIONS

Abstract, CA107(25):235609x; R. A. Sawicki, Triphase Catalysis In Organometallic Anion Chemistry, ACS Symp. Ser., 326, 143–54 (1987).
Abstract, CA92(1):6320a; Y. Kawabata, M. Tanaka, T. Hayashi, I. Ogata, Hydroesterification of Oxiranes Over Cobalt Carbonyl Catalysts, Nippon Kagaku Kaishi, (5), 635–40 (1979).

*Primary Examiner*—Jose' G. Dees
*Assistant Examiner*—Joseph M. Conrad, III

[57] ABSTRACT

The invention relates a process for the carbonylation of epoxides by reaction with carbon monoxide in the presence of a catalyst system containing a source of cobalt and a hydroxy substituted pyridine compound, whereby $\beta$-propiolactones and/or derivatives thereof, such as $\beta$-propiolactone polymers, $\beta$-hydroxy carboxylic acids and esters, and $\beta$-alkoxy carboxylic acids and esters, are produced.

5 Claims, No Drawings

CARBONYLATION OF EPOXIDES

This is a division of application Ser. No. 082,211, filed Jun. 24, 1993 U.S. Pat. No. 5,310,948.

FIELD OF INVENTION

This invention relates to a process for the carbonylation of epoxides. In one aspect, the invention relates to reacting epoxides with carbon monoxide in the presence of an improved catalyst system.

BACKGROUND OF THE INVENTION

It is known that epoxides may be carbonylated by reaction with carbon monoxide. The primary product of the carbonylation reaction is a $\beta$-propiolactone formed by insertion of a carbonyl group into a carbon oxygen bond of the oxirane group of the epoxide. Secondary products, such as $\beta$-propiolactone polymers, 3-hydroxycarboxylic acids and esters, and acrylic acids and esters, may also be formed directly or indirectly under specific conditions due to the reactive nature of the primary $\beta$-propiolactone product.

According to GB-A-1020575 the carbonylation reaction requires the presence of a metal carbonyl catalyst such as a cobalt carbonyl catalyst. In GB-1020575, using ethylene oxide as substrate, $\beta$-propiolactone is obtained as primary product, whereas the presence of metal halides or quaternary ammonium halides promoted the formation of $\beta$-propiolactone polymer. It further discloses that the tendency of 1,2-epoxides to homopolymerize may be diminished by adding a small proportion of a base, such as pyridine, to the reaction mixture.

U.S. Pat. No. 3,260,783 discloses reacting ethylene oxide with carbon monoxide in anhydrous alcoholic solution. This process uses a cobalt carbonyl catalyst, which preferably is modified by a tertiary phosphine or tertiary amine co-catalyst including N-heterocycles such as pyridine and methylpyridine. A similar process is disclosed by Y. Kawabata, et al., in Nippon Kagaku Kaishi, (5), 635-40 (1979).

U.S. Pat. No. 2,782,226 discloses a process where ethylene oxide is allowed to react with carbon monoxide and water in the presence of cobalt on kieselguhr catalyst to form monoethylene glycol hydracrylate (ethylene glycol monoester of 3-hydroxypropionic acid). The ethylene glycol monoester of 3-hydroxypropionic acid as end product is obtained through the addition of a further ethylene oxide molecule to the intermediate 3-hydroxypropionic acid reaction product.

U.S. Pat. No. 4,209,467 discloses catalyst which is a reaction product of a cobalt carbonyl compound and a hydroxy substituted pyridine compound, which are used in the hydroformylation of olefins to aldehydes.

While it is known that epoxides can be carbonylated to produce $\beta$-propiolactones and derivatives, the exemplified catalyst systems leave room for improvement in terms of achievable selectivity and reaction rate in order to arrive at an industrially competitive process.

It is therefore an object of the present invention to provide an epoxide carbonylation process with improved selectivity and/or reaction rate to produce $\beta$-propiolactones and/or derivatives thereof.

SUMMARY OF THE INVENTION

According to the invention, a process for the carbonylation of epoxides is provided comprising reacting an epoxide with carbon monoxide in the presence of a catalyst system comprising a source of cobalt and a hydroxyl-substituted pyridine compound. Further, the reaction may be carried out in the presence of a hydroxyl compound.

A process for the preparation of $\alpha,\beta$-unsaturated carboxylic acids or derivatives thereof is also provided comprising dehydrating the $\beta$-propiolactone monomer or polymer produced from the epoxide carbonylation process.

DETAILED DESCRIPTION OF THE INVENTION

It has now been found that by using a specific catalyst system containing a source of cobalt in conjunction with a hydroxyl-substituted pyridine compound, the present invention provides a much higher selectivity to the $\beta$-propiolactone product compared with the previously used unsubstituted pyridine. The $\beta$-propiolactone products include $\beta$-propiolactones and/or derivatives thereof such as $\beta$-propiolactone polymers, $\beta$-hydroxy carboxylic acids and esters, and $\beta$-alkoxy carboxylic acids and esters. When using a preferred 3-hydroxy substituted pyridine compound, the carbonylation reaction additionally proceeds at a dramatically increased rate.

The metal component of the catalyst system can be a conventional cobalt catalyst. It may be introduced into the reaction in the form of any source of cobalt, which is converted into the catalytically active species under carbon monoxide pressure applied in the process. A very preferable source of cobalt is dicobalt octacarbonyl and/or other cobalt carbonyls. Cobalt salts, such as cobalt acetate may be used as catalyst precursors, as they can be readily carbonylated under carbon monoxide pressure. When adding finely-divided cobalt metal to the reaction mixture for preparing cobalt carbonyls in situ, careful control of temperature will be required for avoiding undesired side reactions. Generally, the cobalt catalyst or precursor will be soluble in the reaction medium. However, the catalyst may also be used in a heterogenized form that would allow for a gaseous reaction medium. The cobalt source may be added in the form of a pre-formed complex with the required hydroxylpyridine compound.

The further component of the present catalyst system is a pyridine compound carrying at least one hydroxyl group substituent. The expression "pyridine compound" is meant here to encompass any compound comprising the pyridine nucleus, i.e. a six-membered heteroaromatic ring containing an imino nitrogen atom. Therefore, multi-ring compounds such as quinoline and 4,4'-bipyridyl can be used when having a hydroxyl substituent. Besides the essential hydroxyl substituent, the pyridine ring may carry further substituents, which do not interfere with the carbonylation reaction.

Representative examples of suitable hydroxyl substituted pyridine compounds include 2-hydroxypyridine, 3-hydroxypyridine, 4-hydroxypyridine, 3,4-dihydroxypyridine, 3-hydroxyquinoline, 4-hydroxy-2-methylpyridine, and 3-hydroxy-4-methylpyridine. The best results were obtained using 3-hydroxy substituted pyridine compounds, which therefore are preferred, in particular 3-hydroxypyridine.

The ratio of hydroxyl substituted pyridine compound to cobalt in the present catalyst systems is not critical and may vary within wide limits. Practical ratios are within the range of from about 0.5 to about 20 moles of hydroxy substituted pyridine compound per gram atom of cobalt, with ratios within the range of from 1 to 5 moles of hydroxyl substituted pyridine compound per gram atom of cobalt being preferred.

The substrates being subjected to carbonylation in accordance with the present invention are epoxides which can be derived from addition of an oxygen atom to an olefinic double bond to form an oxirane ring. The oxirane ring may be substituted with alkyl groups, as in propylene oxide, or other groups, as in styrene oxide. Preferably, the epoxide substrate is an 1,2-epoxide, in particular an optionally substituted 1,2-epoxyalkane. Representative epoxides include ethylene oxide, propylene oxide, styrene oxide, 1,2-epoxyhexane, and 1,2-epoxyoctane.

When the epoxide is reacted with carbon monoxide in the absence of further reactants, the primary product is a β-propiolactone, which may be substituted at the α- and/or β-position, if the starting epoxide constitutes a substituted oxirane. For example, β-butyrolactone [β-methyl-β-propiolactone or 2-oxo-4-methyloxetane] is obtained as product of the carbonylation of propylene oxide, whereas β-propiolactone is the product of the carbonylation of ethylene oxide. Due to the tendency of β-propiolactones to polymerize, the reaction mixture may contain a certain proportion of β-propiolactone polymer, the amount of which slowly increases upon standing. If desired, the direct yield of polymer may be increased by the addition of promoters to the reaction system. Examples of such promoters are metal halides and quaternary ammonium halides, which may be used in a proportion of from 0.10 to 5.0% wt of the epoxide.

The carbonylation reaction is conveniently carried out in a liquid phase. If the epoxide substrate and lactone product are liquid, there is no need for using a separate solvent. However, the use of a separate solvent may be convenient and preferred for practical purposes, for example, in connection with product recovery. Suitable solvents include moderately polar aprotic solvents, in particular ethers such as diglyme (2,5,8-trioxanonane), diphenylether, tetrahydrofuran (THF) and anisole. Protic solvents such as alcohols are usable, but may participate in the reaction to yield other products.

The temperature and pressure for the carbonylation reaction are not critical and may vary within wide limits. It is an advantageous feature of the invention that the reaction may be conducted at mild conditions. The reaction is generally carried out at elevated temperatures and pressures. Preferable temperatures are within the range of from about 50° C. to about 150° C., more preferably from about 60° C. to about 100° C. At lower temperatures the reaction may be unduly retarded, whereas at higher temperatures the formation of secondary derivatives may be induced. Typical pressures are below about 150 bar, as higher pressures would involve excessive equipment cost. Preferred pressures are within the range of about 20-100 bar.

The β-propiolactone product can be recovered as such using conventional separation technology. It may also be recovered in the form of its polymer. The optionally substituted β-propiolactones obtained containing a strained four-member ring readily undergo ring cleavage reactions. They may thermally polymerize to form polyesters of the AB-type. Reaction with alcohols under acidic conditions provides β-alkoxy carboxylic acids, whereas under alkaline conditions β-hydroxy carboxylic acid esters are obtained. By the use of sodium alkoxylates as alkaline material β-alkoxy carboxylic acid esters are directly accessible. Reaction with water provides β-hydroxy carboxylic acids.

Moreover, the β-propiolactones, particularly when substituted at the β-position, or their polymers, show a marked tendency to dehydrate to yield acrylic type of products. For example, it is known that β-lactone polymers on pyrolysis at temperatures within the range of from about 180° to about 250° C. in the presence of a polymerization inhibitor give good yields of α,β-unsaturated carboxylic acids. When heated with an alcohol in the presence of a dehydrating agent, α,β-unsaturated esters can be made.

Accordingly, the present β-propiolactone products constitute versatile precursors to various β-propiolactone derivatives, which in turn are useful and find applications as chemical solvents or as intermediates for further chemical derivatives or polymers. Such derivative products may directly be produced by conducting the present carbonylation process in the presence of a suitable coreactant such as a hydroxyl compounds. For example, when using an alcohol as coreactant, the product of the carbonylation reaction is a β-hydroxy carboxylic acid ester, and using water as coreactant a β-hydroxy carboxylic acid is obtained. Further, for example, the reaction of ethylene oxide with carbon monoxide and methanol in the presence of a catalyst system containing cobalt carbonyl and 3-hydroxypyridine yields the methyl ester of 3-hydroxypropionic acid with excellent selectivity. It will be appreciated that a coreactant such as an alcohol may also act as the solvent for the reaction.

ILLUSTRATIVE EMBODIMENTS

The invention will be further illustrated by the following non-limiting examples.

EXAMPLES 1-4 AND COMPARATIVE EXAMPLE A

Each time a 250 ml stainless-steel autoclave was charged with 10 ml ethylene oxide, 40 ml diglyme, 1 mmol dicobalt octacarbonyl [$CO_2(CO)_8$] and 4 mmol of a pyridine compound as indicated, under exclusion of ambient oxygen. Then the autoclave was pressurized with 60 bar of carbon monoxide and heated for the indicated periods at the indicated temperatures. At the end of the reaction period, the autoclave was cooled and a sample of its content was analyzed by standard gas liquid chromatography (GLC) and $^{13}C$ NMR spectroscopy. The results of the experiments are summarized in Table 1 below in which the conversion is expressed as the percentage of ethylene oxide being converted, the selectivity represents the molar percentage of β-propiolactone formed relative to the total amount of converted ethylene oxide, and the turnovers represent the reaction rate expressed as mole of ethylene oxide converted per gram atom of cobalt per hour.

TABLE 1

| Example No. | Pyridine Compound | T (h) | T (°C.) | Conversion (%) | Selectivity* % | Turnovers (mol/gr at Co/hr) |
|---|---|---|---|---|---|---|
| 1 | 3-hydroxypyridine | 3 | 60 | 100 | >98** | 33 |
| 2 | 3-hydroxypyridine | 1 | 75 | 100 | >98 | 100 |
| 3 | 3-hydroxypyridine | 0.5 | 80 | 100 | >98 | 200 |

TABLE 1-continued

| Example No. | Pyridine Compound | T (h) | T (°C.) | Conversion (%) | Selectivity* % | Turnovers (mol/gr at Co/hr) |
|---|---|---|---|---|---|---|
| 4 | 4-hydroxypyridine | 10 | 75 | 81 | >98 | 10 |
| A (comp) | pyridine | 6 | 75 | 33 | 50 | 8 |

*on standing at room temperature the initially formed lactone, as determined by $^{13}C$ NMR, is slowly converted to polyhydroxypropionate; on injection in GLC pyrolysis to acrylic acid takes place.
**trace of aldehyde.

It can be seen from the Table that the selectivity of the carbonylation reaction is increased by the use of a catalyst system containing hydroxypyridine as proposed by the present invention compared to the use of pyridine. The preferred use of a 3-hydroxy substituted pyridine compound concomitantly enhances the reaction rate as can be seen by comparing Examples 2, 4 and A which are conducted at the same temperature.

EXAMPLE 5

Using the general procedure of Example 1, an autoclave was charged with 20 ml propylene oxide, 40 ml diglyme, 2 mmol of dicobalt octacarbonyl and 4 mmol of 3-hydroxypyridine, and pressurized with 60 bar carbon monoxide. After heating for 6 hours at 75° C., 93% conversion of propylene oxide was observed with a selectivity of >90% into β-butyrolactone (2-oxo-4-methyloxetane).

EXAMPLE 6

Using the general procedure of Example 1, an autoclave was charged with 10 ml isobutylene oxide, 40 ml diglyme, 2 mmol of dicobalt octacarbonyl and 4 mmol of 3-hydroxypyridine, and pressurized to 60 bar carbon monoxide. After heating for 10 hours at 75° C., 60% conversion of isobutylene oxide to 3-hydroxy-3-methylbutanoic acid lactone (2-oxo-4,4-dimethyloxetane) was observed according to $^{13}C$ NMR spectroscopy. 3-hydroxy-3-methylbutanoic acid lactone pyrolysed into 3-methyl-2-butenoic acid upon injection into GLC.

EXAMPLE 7

Using the general procedure of Example 1, an autoclave was charged with 30 ml ethylene oxide, 100 ml diglyme, 2 mmol dicobaltoctacarbonyl and 4 mmol 3-hydroxypyridine, and pressurized to 60 bar carbon monoxide pressure. After heating for 4 hours at 75° C., conversion of ethylene oxide was found to be virtually complete. Upon standing at room temperature for 13 hours a precipitate was formed, which was isolated by filtration and washed with methanol to yield 23 g of poly-3-hydroxypropionate, [—O—CH$_2$—CH$_2$—C(=O)—]$_n$ according to $^{13}C$ NMR spectroscopy.

EXAMPLE 8

Using the general procedure of Example 1, an autoclave was charged with 10 ml ethylene oxide, 40 ml methanol, 1 mmol dicobalt octacarbonyl and 4 mmol 3-hydroxypyridine, and pressurized with 60 bar carbon monoxide. After heating at 75° C. for 4 hours and analysis by GLC, 96% of ethylene oxide was found to have been converted into methyl 3-hydroxypropionate with a selectivity of 97%.

We claim:

1. A process for the preparation of α,β-unsaturated carboxylic acids or derivatives thereof comprising:
   (a) reacting an epoxide with carbon monoxide in the presence of a cobalt-containing catalyst system comprising a source of cobalt and a hydroxyl-substituted pyridine compound thereby producing a β-propiolactone monomer or polymer; and
   (b) dehydrating said β-propiolactone monomer or polymer.

2. The process of claim 1 wherein the dehydration in step (b) is carried out in the presence of a hydroxyl compound.

3. The process of claim 1 wherein the hydroxyl-substituted pyridine compound is a pyridine having the hydroxyl group substituent at the 3-position.

4. The process of claim 1 wherein the epoxide is an 1,2-epoxide.

5. The process of claim 4 wherein the 1,2-epoxide is ethylene oxide or propylene oxide.

* * * * *